US007012099B2

(12) United States Patent
Sundermann et al.

(10) Patent No.: US 7,012,099 B2
(45) Date of Patent: *Mar. 14, 2006

(54) USE OF SUBSTITUTED 4-AMINO-1-PHENYLBUTAN-2-OL COMPOUNDS AS MEDICAMENTS

(75) Inventors: Bernd Sundermann, Aachen (DE); Stephan Wnendt, Aachen (DE); Werner Englberger, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 144 days.

This patent is subject to a terminal disclaimer.

(21) Appl. No.: 10/149,434

(22) PCT Filed: Dec. 20, 2000

(86) PCT No.: PCT/EP00/12975

§ 371 (c)(1),
(2), (4) Date: Jun. 24, 2002

(87) PCT Pub. No.: WO01/47506

PCT Pub. Date: Jul. 5, 2001

(65) Prior Publication Data

US 2003/0008859 A1    Jan. 9, 2003

(30) Foreign Application Priority Data

Dec. 27, 1999  (DE) ................................ 199 63 175

(51) Int. Cl.
*A61K 31/135* (2006.01)
(52) U.S. Cl. ..................................... 514/646; 514/649
(58) Field of Classification Search ................ 514/649, 514/646

See application file for complete search history.

(56) References Cited

U.S. PATENT DOCUMENTS 6,410,790 B1 *   6/2002   Sundermann et al. ....... 564/336

FOREIGN PATENT DOCUMENTS

| EP | 1 043 307 | 10/2000 |
| WO | 92 05169 | 4/1992 |
| WO | 99 46492 | 9/1999 |

OTHER PUBLICATIONS

European Journal of Organic Chemistry (1988), vol. 10, pp. 2185-2191.*
Post-Herpetic Nerualgia: Diagnosis & Treatment, The Pain Management Letter, A quarterly Report on Techniques & Treatmetns in Pain Management, Summer, 1997.*
Neurontin Significantly Reduces Chronic Neuropathic Pain, Doctor's Guide, Dec. 23, 1998, URL:http://www.pslgroup.com/dg/D6AC6.htm.*

R. Ihl et al.: "Zur nootropikabewertung fuer die praxis" NERVENARZT, vol. 68, No. 11, pp. 853-861 Nov. 1997.
R. Bertorelli et al.: "Nociceptin/orphanin FQ and its receptor: a potential target for drug discovery" Trends in Pharmacological Sciences, vol. 21, No. 7, pp. 233-234 Jul. 1, 2000.
D. Moelm, et al., Eur. J. Org. Chem., vol. 10, pp. 2185-2191, "Fragmentation Reactions of Quaternized γ-Amino Alcohols—Diastereoselective Synthesis of Highly Functionalized Oxetanes and Unsaturated Aldehydes and Ketones With a (Z)-C—C Double Bond", 1998.
F. A. Abdulla, et al., The Journal of Neuroscience, vol. 18, No. 23, pp. 9685-9694, "Axotomy Reduces the Effect of Analgesic Opioids Yet Increases the Effect of Nociceptin on Dorsal Root Ganglion Neurons", Dec. 1, 1998.
A. Ardati, et al., Molecular Pharmacology, vol. 51, pp. 816-824, "Interaction of [$^3$H]Orphanin FQ and $^{125}$I-Tyr14-Orphanin FQ With the Orphanin FQ Receptor: Kinetics and Modulation by Cations and Guanine Nucleotides", 1997.
M. Arend, et al., SYNLETT, pp. 974-976, "A Simple and Highly Diastereoselective One-Pot Synthesis of Mannich-Bases", Aug. 1997.
R. Carlson, et al., Acta Chemica Scandinavica B, vol. 38, pp. 49-53, "Improved Titanium Tetrachloride Procedure for Enamine Synthesis. II. Scope of the Reaction", 1984.
H. C. Champion, et al., Biochemical and Biophysical Research Communications, vol. 234, No. 2, pp. 309-312, "[Tyr$^1$]-Nociceptin, a Novel Nociceptin Analog, Decreases Systemic Arterial Pressure by a Naloxone-Insensitive Mechanism in the Rat", 1997.
M. Connor, et al., British Journal of Pharmacology, vol. 118, pp. 205-207, "The Effect of Nociceptin on Ca$^{2+}$Channel Current and Intracellular Ca$^{2+}$in the SH-SY5Y Human Neuroblastoma Cell Line", 1996.
T. Darland, et al., TINS, vol. 21, No. 5, pp. 215-221, "Orphanin FQ/Nociceptin: A Role in Pain and Analgesia, But So Much More", 1998.
E. S. L. Faber, et al., British Journal of Phamacology, vol. 119, pp. 189-190, "Depression of Glutamatergic Transmission by Nociceptin in the Neonatal Rat Hemisected Spinal Cord Preparation in Vitro", 1996.
B. Gumusel, et al., Life Sciences, vol. 60, No. 8, pp. PL-141 to PL-145, "Nociceptin: An Endogenous Agonist for Central Opioid Like$_1$ (ORL$_1$) Receptors Possesses Systemic Vasorelaxant Properties", 1997.

(Continued)

*Primary Examiner*—Kamal A. Saeed
*Assistant Examiner*—Rebecca Anderson
(74) *Attorney, Agent, or Firm*—Oblon, Spivak, McClelland, Maier & Neustadt, P.C.

(57) ABSTRACT

The invention relates to the use of substituted 4-amino-1-phenylbutan-2-ol compounds in the form of their racemates, enantiomers, diastereomers or corresponding bases or corresponding salts of physiologically acceptable acids as regulators for the nociceptin/orphanin-FQ ligand ORL1 receptor system and for the production of medicaments.

6 Claims, No Drawings

OTHER PUBLICATIONS

R. Gutierez, et al., Society for Neuroscience, 28th Ann. Meet., vol. 24, p. 1358, "Inhibition of Kindling Development by Nociceptin/Orphanin FQ", 1998 (Abstract only).

N. Hara, et al., British Journal of Phamacology, vol. 121, pp. 401-408, "Characterization of Nociceptin Hyperalgesia and Allodynia in Conscious Mice", 1997.

G. Helmchen, et al., Methods of Organic Chemistry, vol. E 21 b, pp. 1925-1929, "Stereoselective Synthesis", 1995.

F. Jenck, et al., Proc. Natl. Acad. Sci. USA, vol. 94, pp. 14854-14858, "Orphanin FQ Acts as an Anxiolytic to Attenuate Behavioral Responses to Stress", Dec. 1997.

D. R. Kapusta, et al., Life Sciences, vol. 60, No. 1, pp. PL-15 to PL-21, "Diuretic and Antinatriuretic Responses Produced by the Endogenous Opioid-Like Peptide, Nociceptin (Orphanin FQ)", 1997.

M. A. King, et al., Neuroscience Letters, vol. 223, pp. 113-116, "Spinal Analgesic Activity of Orphanin FQ/Nociceptin and its Fragments", 1997.

F. Knoflach, et al., The Journal of Neuroscience, vol. 16, No. 21, pp. 6657-6664, "Modulation of Voltage-Gated Calcium Channels by Orphanin FQ in Freshly Dissociated Hippocampal Neurons", Nov. 1, 1996.

T. Manabe, et al., Nature, vol. 394, pp. 577-581, "Facilitation of Long-Term Potentiation and Memory in Mice Lacking Nociceptin Receptors", Aug. 6, 1998.

H. Matthes, et al., Molcular Pharmacology, vol. 50, pp. 447-450, "Functional Selectivity of Orphanin FQ for its Receptor Coexpressed With Potassium Channel Subunits in Xenopus Laevis Oocytes", 1996.

J-C. Meunier, et al., Nature, vol. 377, pp. 532-535, "Isolation and Structure of the Endogenous Agonist of Opioid Receptor-Like $ORL_1$ Receptor", Oct. 12, 1995.

J. S. Mogil, et al., Neuroscience Letters, vol. 214, pp. 131-134, "Functional Antagonism of $\mu$-, $\delta$- and $\kappa$-Opioid Antinociception by Orphanin FQ", 1996.

J. S. Mogil, et al., Neuroscience, vol. 75, No. 2, pp. 333-337, "Orphanin FQ is a Functional Anti-Opioid Peptide", 1996.

C. Mollereau, et al., FEBS Letters, vol. 341, pp. 33-38, "ORL1, a Novel Member of the Opioid Receptor Family Cloning, Functional Expression and Localization", 1994.

M. Nishi, et al., The EMBO Journal, vol. 16, No. 8, pp. 1858-1864, "Unrestrained Nociceptive Response and Disregulation of Hearing Ability in Mice Lacking the Nociceptin/Orphanin FQ Receptor", 1997.

J. D. Pomonis, et al., NeuroReport, vol. 8, No. 1, pp. 369-371, "Orphanin FQ, Agonist of Orphan Opioid Receptor $ORL_1$, Stimulates Feeding in Rats", Dec. 20, 1996.

R. K. Reinscheid, et al., Science, vol. 270, pp. 792-794, "Orphanin FQ: A Neuropeptide that Activates an Opioidlike G Protein-Coupled Receptor", Nov. 3, 1995.

N. Risch, et al., Angew. Chem., vol. 106, No. 23-24, pp. 2531-2533, "Diastereomerenreine Mannich-Basen Durch Addition Von Enaminen An Ternaere Iminiumsalze", 1994.

J. Sandin, et al., European Journal of Neuroscience, vol. 9, pp. 194-197, "Short Communication Nociceptin-Orphanin FQ Microinjected into Hippocampus Impairs Spatial Learning in Rats", 1997.

Y.-S. Shu, et al., Neuropeptides, vol. 32, No. 6, pp. 567-571, "Orphanin FQ/Nociceptin Modulates Glutamate- and Kainic Acid-Induced Currents in Acutely Isolated Rat Spinal Dorsal Horn Neurons", 1998.

C. W. Vaughan, et al., British Journal of Phamacology, vol. 117, pp. 1609-1611, "Increase by the $ORL_1$ Receptor (Opioid Receptor-Like$_1$) Ligand, Nociceptin, of Inwardly Rectifying K Conductance in Dorsal Raphe Nucleus Neurones", 1996.

E. Winterfeldt, Synthesis, pp. 617-630, "Applications of Diisobutylaluminium Hydride (Dibah) and Triiso-Butylaluminium (Tiba) as Reducing Agents in Organic Synthesis", Oct. 1975.

X-J. Xu, et al., NeuroReport, vol. 7, No. 13, pp. 2092-2094, "Nociceptin or Antinociceptin: Potent Spinal Antinociceptive Effect of Orphanin FQ/Nociceptin in the Rat", Sep. 2, 1996.

T. Yamamoto, et al., Neuroscience, vol. 81, No. 1, pp. 249-254, "Analgesic Effect of Intrathecally Administered Nociceptin, an Opioid Receptor-Like$_1$ Receptor Agonist, in the Rat Formalin Test", 1997.

T. Yamamoto, et al., Anesthesiology, vol. 87 No. 5, pp. 1145-1152, "Effects of Intrathecally Administered Nocicepin, an Opioid Receptor-Like$_1$ Receptor Agonist, and N-Methyl-D-Aspartate Receptor Antagonists on the Thermal Hyperalgesia Induced by Partial Sciatic Nerve Injury in the Rat", Nov. 1997.

* cited by examiner

USE OF SUBSTITUTED 4-AMINO-1-PHENYLBUTAN-2-OL COMPOUNDS AS MEDICAMENTS

This application is a 371 of PCT/EP00/12975 filed Dec. 20, 2000.

This invention relates to the use of substituted 4-amino-1-phenylbutan-2-ol compounds in the form of their racemates, enantiomers, diastereoisomers or corresponding bases or corresponding salts of physiologically tolerable acids as regulators for the nociceptin/orphanin FQ ligand-ORL1 receptor system and in the preparation of medicaments.

The heptadecapeptide nociceptin/orphanin FQ is an endogenous ligand of the ORL1 (opioid-receptor-like) receptor (Meunier et al., Nature 377, 1995, p. 532–535), which belongs to the family of the opioid receptors and is to be found in many regions of the brain and of the spinal cord (Mollereau et al., FEBS Letters, 341, 1994, p. 33–38, Darland et al., Trends in Neurosciences, 21, 1998, p. 215–221). The peptide is characterised by a high affinity, with a $K_d$ value of approximately 56 pM (Ardati et al., Mol. Pharmacol. 51, p. 816–824), and by a high degree of selectivity for the ORL1 receptor. The ORL1 receptor is homologous to the $\mu$, $\kappa$ and $\delta$ opioid receptors and the amino acid sequence of the nociceptin/orphanin FQ peptide has a strong similarity with those of the known opioid peptides. Activation of the receptor, induced by nociceptin/orphanin FQ, leads, via coupling with $G_{I/O}$ proteins, to inhibition of adenylate cyclase (Meunier et al., Nature 377, 1995, p. 532–535). Functional similarities of the $\mu$, $\kappa$ and $\delta$ opioid receptors with the ORL1 receptor in respect of activation of the potassium channel (Matthes et al., Mol. Pharmacol. 50, 1996, p. 447–450; Vaughan et al., Br. J. Pharmacol. 117, 1996, p. 1609–1611) and inhibition of the L-, N- and P/Q-type calcium channels are also present at cell level (Conner et al., Br. J. Pharmacol. 118, 1996, p. 205–207; Knoflach et al., J. Neuroscience 16, 1996, p. 6657–6664).

Following intercerebroventicular administration, the nociceptin/orphanin FQ peptide exhibits pro-nociceptive and hyperalgesic activity in various animal models (Reinscheid et al., Science 270, 1995, p. 792–794, Hara et al., Br. J. Pharmacol. 121, 1997, p. 401–408). These results can be explained as inhibition of stress-induced analgesia (Mogil et al., Neurosci. Letters 214, 1996, p.131–134; and Neuroscience 75, 1996, p. 333–337). In this connection, it has also been possible to demonstrate an anxiolytic activity of the nociceptin/orphanin FQ peptide (Jenck et al., Proc. Natl. Acad. Sci. USA 94, 1997, 14854–14858).

On the other hand, it has also been possible in various animal models to show an anti-nociceptive effect of nociceptin/orphanin FQ, especially following intrathecal administration. Nociceptin/orphanin FQ inhibits the activity of kainate- or glutamate-stimulated dorsal root ganglia neurons (Shu et al., Neuropeptides, 32, 1998, p. 567–571) or glutamate-stimulated spinal cord neurons (Faber et al., Br. J. Pharmacol., 119, 1996, p. 189–190); it has an anti-nociceptive action in the tail-flick test in mice (King et al., Neurosci. Lett., 223, 1997, 113–116), in the flexor reflex model in rats (Xu et al., NeuroReport, 7, 1996, 2092–2094) and in the formalin test in rats (Yamamoto et al., Neuroscience, 81, 1997, p. 249–254). An anti-nociceptive activity for nociceptin/orphanin FQ could also be demonstrated in models for neuropathic pain (Yamamoto and Nozaki-Taguchi, Anesthesiology, 87, 1997), which is particularly interesting in so far as the effectiveness of nociceptin/orphanin FQ increases after axotomy of spinal nerves. That is in contrast with the conventional opioids, the effectiveness of which falls under those conditions (Abdulla and Smith, J. Neurosci., 18, 1998, p. 9685–9694).

The nociceptin/orphanin FQ ligand-ORL1 receptor system is additionally involved in the regulation of other physiological and pathophysiological processes. These include, inter alia, learning and memory formation (Sandin et al., Eur. J. Neurosci., 9, 1997, p. 194–197; Manabe et al., Nature, 394,1997, p. 577–581), hearing ability (Nishi et al., EMBO J., 16, 1997, p.1858–1864), food intake (Pomonis et al., NeuroReport, 8, 1996, p. 369–371), regulation of blood pressure (Gumusel et al., Life Sci., 60, 1997, p. 141–145; Campion and Kadowitz, Biochem. Biophys. Res. Comm., 234, 1997, p. 309–312), epilepsy (Gutiérrez et al., Abstract 536.18, Society for Neuroscience, Vol. 24, 28th Ann. Meeting, Los Angeles, Nov. 7–12, 1998) and diuresis (Kapista et al., Life Sciences, 60, 1997, PL 15–21).

The object of the present invention was to make available medicaments that act on the nociceptin/orphanin FQ ligand-ORL1 receptor system and accordingly are suitable for the treatment of depression and/or hypotension and/or hypertension and/or senile dementia and/or Alzheimer's disease and/or general cognitive dysfunctions and/or tinnitus and/or hardness of hearing and/or epilepsy and/or obesity and/or cachexia and/or for anxiolysis and/or for diuresis.

It has been found that substituted 4-amino-1-phenylbutan-2-ol compounds of the general formula I below exhibit an effect on the control of various physiological and pathophysiological processes in which the nociceptin/orphanin FQ ligand-ORL1 receptor system is involved. The mentioned processes include, inter alia, anxiety behaviour, learning and memory formation, regulation of blood pressure, hearing, food intake, epilepsy and diuresis.

Accordingly, the present invention relates to the use of at least one substituted 4-amino-1-phenylbutan-2-ol compound of the general formula I

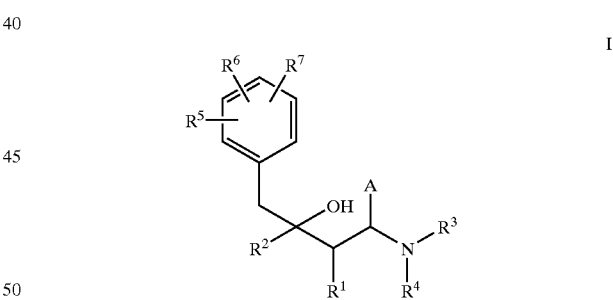

wherein the radical A represents an aryl or heteroaryl radical, the radicals $R^1$ and $R^2$, which may be identical or different, represent a $C_{1-6}$-alkyl radical, preferably a $C_{1-3}$-alkyl radical, or $R^1$ and $R^2$ together form a $(CH_2)_{2-6}$ ring, which may also be substituted by phenyl, the radicals $R^3$ and $R^4$, which may be identical or different, represent a $C_{1-6}$-alkyl radical, preferably a $C_{1-3}$-alkyl radical, an aryl radical, or an aryl radical bonded via a $C_{1-3}$-alkylene group, or the radicals $R^3$ and $R^4$ together represent $(CH_2)_{3-6}$ or $CH_2CH_2OCH_2CH_2$, the radicals $R^5$, $R^6$ and $R^7$, which may be identical or different, represent H, F, Cl, Br, I, $CF_3$, $OR^8$, $SO_2CH_3$, $SO_2CF_3$, phenyl, CN, $NO_2$ or a $C_{1-6}$-alkyl radical, the radical $R^8$ represents H, a $C_{1-6}$-alkyl radical, preferably a $C_{1-3}$-alkyl radical, an aryl radical, a heteroaryl radical, or an aryl or heteroaryl radical bonded via a $C_{1-3}$-alkylene group, in the form of its racemate, its enantiomers, its diastereoisomers or corresponding bases or corresponding salts of physiologically tolerable acids, as a regulator for the nociceptin/orphanin FQ ligand-ORL1 receptor system.

Alkyl radicals are to be understood as being also branched, unbranched and cyclic hydrocarbons, which may also be substituted at least once, preferably by a halogen and/or a hydroxyl radical, especially by fluorine and/or a hydroxyl radical. If more than one substituent is present, then the substituents may be identical or different. Preference is given to the alkyl radicals methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, cyclopropylmethyl, 2-methylcyclopropyl, cyclopentyl, cyclohexyl, $CHF_2$, $CF_3$ or $CH_2OH$.

An aryl radical is to be understood as being also phenyl or naphthyl radicals substituted at least once by an $OR^8$ radical, a halogen radical, preferably F and/or Cl, a CN radical, an $NO_2$ radical, a $C_{1-6}$-alkyl radical or by a phenyl radical, the radical $R^8$ being as defined above. The phenyl radicals may also be condensed with further rings.

A heteroaryl radical is to be understood as being also 5- or 6-membered, unsaturated heterocyclic compounds optionally containing a system of fused aryl radicals, which heterocyclic compounds contain at least one hetero atom, preferably nitrogen, oxygen and/or sulfur, especially nitrogen and/or oxygen, and may also optionally be substituted at least once by an $OR^8$ radical, a halogen radical, preferably F and/or Cl, a CN radical, an $NO_2$ radical, a $C_{1-6}$-alkyl radical or by a phenyl radical, the radical $R^8$ being as defined above. The heteroaryls are preferably furan, thiophene, pyrrole, pyridine, pyrimidine, quinoline, isoquinoline, phthalazine or quinazoline.

Preference is given to substituted 4-amino-1-phenylbutan-2-ol compounds of the general formula I in which $R^1$ and $R^2$ together form a $(CH_2)_{2-6}$ ring, which may also be substituted by phenyl, and $R^3$ to $R^8$ and A are as defined according to the general formula I.

Preference is given also to substituted 4-amino-1-phenylbutan-2-ol compounds of the general formula I in which A represents a phenyl, thiophenyl or furyl radical that is unsubstituted or is substituted at least once, preferably by $OR^8$, an F, Cl, Br radical, a CN radical, an $NO_2$ radical, a $C_{1-6}$-alkyl radical or by a phenyl radical, and $R^1$ to $R^8$ are as defined according to the general formula I.

Also preferred are compounds of the general formula I in which $R^5$ to $R^7$ each independently of the others represent H, a halogen radical or a $CF_3$ radical, and $R^1$ to $R^4$ are as defined according to the general formula I.

Special preference is given to compounds of the general formula I in which $R^1$ and $R^2$ together form a cyclohexyl ring, which may also be substituted by phenyl, A represents a phenyl, thiophenyl or furyl radical that is unsubstituted or is substituted at least once, preferably by $OR^8$, an F, Cl, Br radical, a CN radical, an $NO_2$ radical, a $C_{1-6}$-alkyl radical or by a phenyl radical, and $R^3$ to $R^8$ are as defined according to the general formula I.

Very special preference is given to the following 4-amino-1-phenylbutan-2-ol compounds:
1-(2-chlorobenzyl)-2-(dimethylaminophenylmethyl)cyclohexanol and the corresponding hydrochloride
1-(3-chlorobenzyl)-2-(dimethylaminophenylmethyl)cyclohexanol and the corresponding hydrochloride
1-(4-chlorobenzyl)-2-(dimethylaminophenylmethyl)cyclohexanol and the corresponding hydrochloride
1-(3,4-difluorobenzyl)-2-(dimethylaminophenylmethyl)cyclohexanol and the corresponding hydrochloride
2-(dimethylaminophenylmethyl)-1-(3-trifluoromethylbenzyl)cyclohexanol and the corresponding hydrochloride
2-(dimethylaminothiophen-2-ylmethyl)-1-(3-trifluoromethylbenzyl)cyclohexanol and the corresponding hydrochloride
2-(dimethylaminothiophen-3-ylmethyl)-1-(3-trifluoromethylbenzyl)cyclohexanol and the corresponding hydrochloride.

The invention relates also to the use of at least one substituted 4-amino-1-phenylbutan-2-ol compound of the general formula I as a regulator for the nociceptin/orphanin FQ ligand-ORL1 receptor system in the preparation of a medicament for the treatment of depression and/or hypotension and/or hypertension and/or senile dementia and/or Alzheimer's disease and/or general cognitive dysfunctions and/or tinnitus and/or hardness of hearing and/or epilepsy and/or obesity and/or cachexia and/or for anxiolysis and/or for diuresis.

The invention further relates to the use of at least one substituted 4-amino-1-phenylbutan-2-ol compound of the general formula I in the preparation of a medicament for the treatment of depression and/or hypotension and/or hypertension and/or senile dementia and/or Alzheimer's disease and/or general cognitive dysfunctions and/or tinnitus and/or hardness of hearing and/or epilepsy and/or obesity and/or cachexia and/or for anxiolysis and/or for diuresis.

For the preparation of corresponding pharmaceutical formulations, carriers, fillers, solvents, diluents, colouring agents and/or binders are used in addition to at least one 4-amino-1-phenylbutan-2-ol compound of the general formula I. The choice of excipients and the amounts thereof to be used are dependent on whether the medicament is to be administered by the oral, intravenous, intraperitoneal, intradermal, intramuscular, intranasal, buccal or topical route. Preparations in the form of tablets, dragées, capsules, granules, drops, juices and syrups are suitable for oral administration; solutions, suspensions, readily reconstitutable dry preparations and also sprays are suitable for administration parenterally, topically and by inhalation. The compounds of the general formula I in depot form, in dissolved form or in a plaster, optionally with the addition of agents that promote penetration of the skin, are suitable percutaneous forms of administration. Forms of administration for oral or percutaneous use may release the compounds of the general formula I in a delayed manner.

Physiologically tolerable salts of the 4-amino-1-phenylbutan-2-ol compounds of the general formula I and/or their enantiomers and/or their diastereoisomers which may be used are preferably the hydrochlorides, hydrobromides, sulfates, sulfonates, phosphates, tartrates, embonates, formates, acetates, propionates, benzoates, oxalates, succinates, citrates, glutamates, fumarates, aspartates, glutarates, stearates, butyrates, malonates, lactates, mesylates, or a mixture of at least two of those salts.

The amount of active ingredient to be administered to the patient varies in dependence on the weight of the patient, the type of administration, the indication and the degree of severity of the disease. There are usually administered from 0.5 to 50 mg/kg body weight of the patient of at least one 4-amino-1-phenylbutan-2-ol compound of the general formula I.

The substituted 4-amino-1-phenylbutan-2-ol compounds of the general formula I have been prepared by the following processes, the radicals $R^1$ to $R^7$ and A being as defined according to the general formula I.

Reaction of Mannich bases of the general formula II

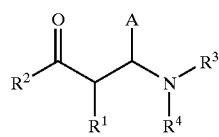

II with substituted benzyl Grignard compounds of the general formula III

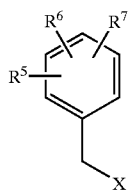

III wherein X=MgCl, MgBr, MgI or Li, in an aliphatic ether, preferably diethyl ether and/or tetrahydrofuran, a hydrocarbon, preferably hexane or toluene, or mixtures of hydrocarbons and aliphatic ethers, preferably at temperatures from −70° C. to +110° C., yielded, in dependence on the reaction conditions, preferably tertiary alcohols having the relative configuration of the general formula Ia

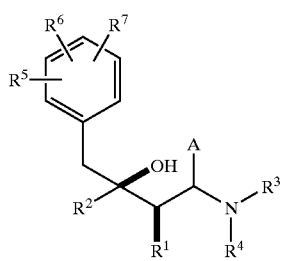

Ia in which the aminoarylmethyl or aminoheteroarylmethyl group is arranged in the cis configuration with respect to the hydroxyl group when $R^1$ and $R^2$ form a ring system. In the case of open-chain systems, the analogous relative stereochemistry is obtained, which is to be specified as the anti configuration. The compounds of the general formula Ia can be obtained in diastereoisomerically pure form by separation by column chromatography or by crystallisation of their salts, for example of the hydrochlorides.

The Mannich bases of the general formula II can be obtained according to processes known in the literature (Houben-Weyl-Methoden der Organischen Chemie, E21 b, 1995, p. 1925–1929), by reacting enamines of the general formula IV

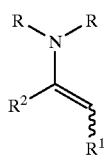

IV with an iminium salt of the general formula V

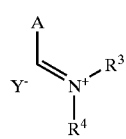

V wherein Y preferably represents Cl⁻, AlCl$_4^-$, Br⁻ or I⁻.

The enamines of the general formula IV are obtained according to processes known in the literature by reacting ketones of the general formula VI

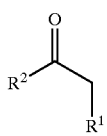

VI with secondary amines, preferably dimethylamine, pyrrolidine, piperidine or morpholine (Acta Chem. Scand. B 38, 1984, p. 49–53). The iminium salts of the general formula V are prepared according to processes known in the literature by reacting aminals of the general formula VII

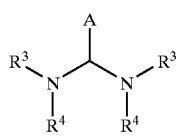

VII with acid chlorides, for example acetyl chloride or thionyl chloride (Houben-Weyl-Methoden der Organischen Chemie, E21b, 1995, p. 1925–1929). The iminium salts of the general formula V do not have to be isolated but can be produced in situ and reacted with enamines of the general formula IV to form Mannich bases of the general formula II (Angew. Chem. 106, 1994, p. 2531–2533). Owing to the fact that the enamine-imine tautomerism is analogous to the keto-enol tautomerism, it is possible to use instead of the enamines of the general formula IV also imines of the general formula VIII

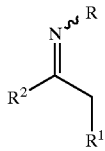

VIII

Alternatively, ketones of the general formula VI may also be reacted directly with iminium salts of the general formula V.

Mannich bases of the general formula II may, however, also be prepared directly by reacting enamines of the general formula IV with an aromatic or heteroaromatic aldehyde of the general formula IX

IX and a secondary amine of the general formula $HNR^3R^4$ (XI), also in the form of the corresponding hydrochloride $HNR^3R^4$·HCl, preferably in the presence of triethylamine, chlorotrimethylsilane and sodium iodide (Synlett 1997, p. 974–976).

By means of the above-described processes, the Mannich bases of the general formula II are obtained, in dependence on the reaction conditions, preferably with the relative configuration of the general formula IIa

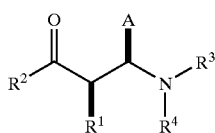

IIa in which the amino group is arranged in the anti configuration with respect to $R^1$. Those compounds of the general formula IIa can be obtained in diastereoisomerically pure form by crystallisation, also of their salts, for example of the hydrochlorides, or by separation by chromatography.

On the other hand, the preparation of Mannich bases of the general formula II by the 1,4-addition of secondary amines of the general formula XI to enones of the general formula X

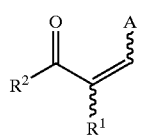

X which are obtained from the aldol condensation of ketones of the general formula VI with aromatic or heteroaromatic aldehydes of the general formula IX, proceeds in a less stereoselective manner (U.S. Pat. No. 4,017,637). Accordingly, that procedure is suitable for the preparation of the other possible stereoisomers.

If chiral amines are used for the preparation of enamines of the general formula IV or imines of the general formula VIII, then enantiomerically enriched to enantiomerically pure Mannich bases of the general formula II can be obtained in the subsequent Mannich reaction (Houben-Weyl-Methoden der Organischen Chemie, E21b, 1995, p. 1925–1929).

4-Amino-1-phenylbutan-2-ol compounds of the general formula I that contain a phenol may preferably be prepared from the corresponding methyl ether compounds using diisobutylaluminium hydride in an aromatic hydrocarbon, preferably toluene, at a temperature from 60 to 130° C. (Synthesis 1975, p. 617–630).

The 4-amino-1-phenylbutan-2-ol compounds of the general formula I have been studied in a receptor binding assay using $^3$H-nociceptin/orphanin FQ with membranes of recombinant CHO-ORL1 cells. That test system was carried out according to the method put forward by Ardati et al. (Mol. Pharmacol., 51, 1997, p. 816–824). The concentration of $^3$H-nociceptin/orphanin FQ in those tests was 0.5 nM. The binding assays were carried out using in each case 20 µg of membrane protein per 200 µl batch in 50 mM Hepes, pH 7.4, 10 mM $MgCl_2$ and 1 mM EDTA. Binding to the ORL1 receptor was determined using in each case 1 mg of WGA-SPA beads (Amersham-Pharmacia, Freiburg) by incubation of the batch for one hour at room temperature and subsequent measurement in a Trilux scintillation counter (Wallac, Finland). The affinity is given as the $K_i$ value.

The Examples which follow serve to illustrate the invention but do not limit the general concept of the invention.

EXAMPLES

The yields of the compounds prepared are not optimised. All temperatures are uncorrected.

Silica gel 60 (0.040–0.063 mm) from E. Merck, Darmstadt, was used as the stationary phase for column chromatography.

Investigations by thin-layer chromatography were carried out using HPTLC precoated plates, silica gel 60 F 254, from E. Merck, Darmstadt.

The mixing ratios of the eluants for all investigations by chromatography are always given in volume/volume.

Vol. % means percentage by volume and m % means percentage by mass.

The expression room temperature means from 20 to 25° C.

Example 1

1-(2-Chlorobenzyl)-2-(dimethylaminophenylmethyl) cyclohexanol hydrochloride

1st Step

Benzylidenedimethylammonium Chloride 10 g (56 mmol) of N,N,N',N'-tetramethyl-C-phenyl-methanediamine (J. Am. Chem. Soc. 77,1955, p. 1114–1116) were dissolved in 100 ml of diethyl ether and cooled to 0° C. in an ice-bath. 4.0 ml (56 mmol) of acetyl chloride were added dropwise under nitrogen. After the first drops, a white salt was precipitated, the temperature rose slightly. After 15 hours at room temperature, the supernatant liquor was decanted off and the solid was washed three times with 100 ml of diethyl ether each time, filtered over a protective gas frit under nitrogen and dried under an oil-pump vacuum until a constant weight was reached. In that manner, 7.7 g of benzylidenedimethylammonium chloride (corresponding to 81% of the theoretically calculated yield) were obtained.

2nd Step 2-(dimethylaminophenylmethyl)cyclohexanone 7.1 ml (44 mmol) of 1-(pyrrolidino)-1-cyclohexene were dissolved in 45 ml of dichloromethane and cooled to −70° C., under nitrogen, with a dry ice/isopropanol bath. 7.5 g (44 mmol) of benzylidenedimethylammonium chloride from step 1 were added with stirring, and the mixture was warmed to −30° C. in the course of from two to three hours and stored at that temperature for 15 hours.

For working up, 60 ml of semi-concentrated hydrochloric acid were added and stirring was then carried out for 5 minutes. The mixture was washed at room temperature with 50 ml of diethyl ether; 440 ml of ammonia solution (25 vol. %) were added to the aqueous phase, and the mixture was rapidly extracted three times using 150 ml of diethyl ether each time. The combined organic extracts were dried over sodium sulfate, filtered and concentrated in a rotary evaporator without the supply of heat (from 500 to 10 mbar). In that manner, 10.1 g of crude base (corresponding to 99.5% of the theoretically calculated yield) were obtained. 9.81 g (42.4 mmol) of the crude base were dissolved in 83 ml of 2-butanone, and 0.76 ml (42.2 mmol) of water and 5.36 ml (42.4 mmol) of chlorotrimethylsilane were added in succession. The batch was stored at room temperature for 15 hours, and the resulting solid was filtered off with suction, washed with small portions of diethyl ether and dried under an oil-pump vacuum until a constant weight was reached. In that manner, 8.92 g of the hydrochloride of 2-(dimethylaminophenylmethyl)cyclohexanone (corresponding to 79% of the theoretically calculated yield) were obtained.

3rd Step 1-(2-chlorobenzyl)-2-(dimethylaminophenylmethyl)cyclohexanol hydrochloride 0.38 g (15.6 mmol) of magnesium chips were stirred into 15 ml of analytically pure diethyl ether. 2.0 ml (15.6 mmol) of 2-chlorobenzyl chloride, dissolved in 15 ml of diethyl ether, were added dropwise in such a manner that the reaction mixture boiled slightly. After the addition, stirring was continued for one hour at room temperature. 3.0 g (13.0 mmol) of the 2-(dimethylaminophenylmethyl)cyclohexanone prepared according to step 2 were dissolved in 15 ml of diethyl ether, added dropwise to the Grignard batch while cooling with an ice-bath, and stirred for 15 hours at room temperature.

For working up, 30 ml of saturated ammonium chloride solution were added while cooling with an ice-bath, and the mixture was extracted three times at room temperature using 60 ml of ethyl acetate each time. The combined organic extracts were dried over sodium sulfate, filtered and concentrated in a rotary evaporator (from 500 to 10 mbar). 4.50 g of crude base (corresponding to 97% of the theoretically calculated yield) were obtained, from which a hydrochloride was precipitated according to Example 1 (2nd step) using chlorotrimethylsilane/water in 2-butanone. The base was freed therefrom using 40 ml of water and 5 ml of sodium hydroxide solution (32 m %) and extracted three times using 40 ml of diethyl ether each time, and the combined organic extracts were dried over sodium sulfate, filtered and concentrated in a rotary evaporator (from 500 to 10 mbar). 2.90 g of crude base were obtained and added to a 3.5×15 cm column packed with silica gel. Elution with ethyl acetate/n-hexane 2:5 yielded 1.59 g of base, from which there were obtained according to Example 1 (2nd step), using chlorotrimethylsilane/water in 2-butanone, 1.75 g of 1-(2-chlorobenzyl)-2-(dimethylaminophenylmethyl)cyclohexanol hydrochloride (corresponding to 34% of the theoretically calculated yield), which decomposes at 130° C. and above on heating.

Example 2

1-(3-chlorobenzyl)-2-(dimethylaminophenylmethyl) cyclohexanol hydrochloride 0.38 g (15.6 mmol) of magnesium chips were stirred into 15 ml of analytically pure diethyl ether. 2.0 ml (15.6 mmol) of 3-chlorobenzyl chloride, dissolved in 15 ml of diethyl ether, were added dropwise in such a manner that the reaction mixture boiled slightly. After the addition, stirring was continued for one hour at room temperature. 3.0 g (13.0 mmol) of the 2-(dimethylaminophenylmethyl)cyclohexanone prepared according to Example 1 were dissolved in 15 ml of diethyl ether, added dropwise to the Grignard batch while cooling with an ice-bath, and stirred for 15 hours at room temperature.

For working up, 30 ml of saturated ammonium chloride solution were added while cooling with an ice-bath, and the mixture was extracted three times at room temperature using 60 ml of ethyl acetate each time. The combined organic extracts were dried over sodium sulfate, filtered and concentrated in a rotary evaporator (from 500 to 10 mbar). 4.55 g of crude base (corresponding to 98% of the theoretically calculated yield) were obtained, from which a hydrochloride was precipitated according to Example 1 (2nd step) using chlorotrimethylsilane/water in 2-butanone. The base was freed therefrom using 40 ml of water and 5 ml of sodium hydroxide solution (32 m %) and extracted three times using 40 ml of diethyl ether each time, and the combined organic extracts were dried over sodium sulfate, filtered and concentrated in a rotary evaporator (from 500 to 10 mbar). 2.87 g of crude base were obtained, to which 5 ml of ethyl acetate/n-hexane 2:5 were added. The insoluble residue was filtered off and dried. There were obtained 2.11 g of base, from which there were precipitated according to Example 1 (2nd step), using chlorotrimethylsilane/water in 2-butanone, 1.68 g of 1-(3-chlorobenzyl)-2-(dimethylaminophenylmethyl)cyclohexanol hydrochloride (corresponding to 33% of the theoretically calculated yield) having a melting point of 185–188° C.

Example 3

1-(4-chlorobenzyl)-2-(dimethylaminophenylmethyl)-1-cyclohexanol hydrochloride 0.38 g (15.6 mmol) of magnesium chips were stirred into 15 ml of analytically pure diethyl ether. 1.99 g (15.6 mmol) of 4-chlorobenzyl bromide, dissolved in 15 ml of diethyl ether, were added dropwise in such a manner that the reaction mixture boiled slightly. After the addition, stirring was continued for one hour at room temperature. 3.0 g (13.0 mmol) of the 2-(dimethylaminophenylmethyl)cyclohexanone prepared according to Example 1 were dissolved in 15 ml of diethyl ether, added dropwise to the Grignard batch while cooling with an ice-bath, and stirred for 15 hours at room temperature.

For working up, 30 ml of saturated ammonium chloride solution were added while cooling with an ice-bath, and the mixture was extracted three times at room temperature using 60 ml of ethyl acetate each time. The combined organic extracts were dried over sodium sulfate, filtered and concentrated in a rotary evaporator (from 500 to 10 mbar). 4.48 g of crude base (corresponding to 97% of the theoretically calculated yield) were obtained.

From the crude base there were obtained according to Example 1 (2nd step), using chlorotrimethylsilane/water in 2-butanone, 1.74 g of 1-(4-chlorobenzyl)-2-(dimethylaminophenylmethyl)-1-cyclohexanol hydrochloride (corresponding to 34% of the theoretically calculated yield), which decomposes at 208° C. and above on heating.

Example 4

1-(3,4-difluorobenzyl)-2-(dimethylaminophenylmethyl)cyclohexanol hydrochloride 0.29 g (11.9 mmol) of magnesium chips were stirred into 5 ml of analytically pure diethyl ether. 2.47 g (11.9 mmol) of 3,4-difluorobenzyl bromide, dissolved in 10 ml of diethyl ether, were added dropwise in such a manner that the reaction mixture boiled slightly. After the addition, stirring was continued for one hour at room temperature. 2.30 g (9.9 mmol) of the 2-(dimethylaminophenylmethyl)cyclohexanone prepared according to Example 1 were dissolved in 10 ml of diethyl ether, added dropwise to the Grignard batch while cooling with an ice-bath, and stirred for 15 hours at room temperature.

For working up, 15 ml of saturated ammonium chloride solution were added while cooling with an ice-bath, and the mixture was extracted three times at room temperature using 15 ml of diethyl ether each time. The combined organic extracts were dried over sodium sulfate, filtered and concentrated in a rotary evaporator (from 500 to 10 mbar). 3.58 g of crude base (corresponding to 100% of the theoretically calculated yield) were obtained, from which a hydrochloride was precipitated according to Example 1 (2nd step) using chlorotrimethylsilane/water in 2-butanone. The base was freed therefrom using 30 ml of water and 10 ml of ammonia solution (25 vol. %) and extracted three times using 20 ml of diethyl ether each time, and the combined organic extracts were dried over sodium sulfate, filtered and concentrated in a rotary evaporator (from 500 to 10 mbar). 2.31 g of crude base (65% of the theoretical yield) were obtained, from which there were precipitated according to Example 1 (2nd step), using chlorotrimethylsilane/water in 2-butanone, 2.0 g of 1-(3,4-difluorobenzyl)-2-(dimethylaminophenylmethyl)cyclohexanol hydrochloride (corresponding to 51% of the theoretically calculated yield) having a melting point of 185–188° C.

Example 5

1st Step:
2-(dimethylaminophenylmethyl)cyclohexanone 32.1 g (283 mmol) of freshly dried dimethylamine hydrochloride were added, with stirring, to 620 ml (620 mmol) of sodium iodide solution (1 M in acetonitrile), cooled to 0° C. with an ice-bath; 79 ml (565 mmol) of triethylamine and 79 ml (620 mmol) of chlorotrimethylsilane were added dropwise, and the mixture was then stirred for one hour at room temperature. While cooling with ice, 30.0 g (283 mmol) of benzaldehyde were added, and stirring was carried out for a further one hour at room temperature. The mixture was again cooled to 0° C. with an ice-bath, 42.7 g (283 mmol) of 1-(pyrrolidino)-1-cyclohexene were added, and the mixture was stirred for a further two hours at room temperature.

For working up, 420 ml of semi-concentrated hydrochloric acid were added to the batch while cooling with ice, and the mixture was stirred for 10 minutes, washed twice with 420 ml of diethyl ether each time, and rendered alkaline (pH approximately 9) with 1060 ml of dilute ammonia solution (5 vol. %). The mixture was extracted three times using 420 ml of diethyl ether each time, and the combined organic extracts were dried over sodium sulfate, filtered and concentrated in a rotary evaporator (from 500 to 10 mbar) without the supply of heat. 54.1 g of 2-(dimethylaminophenylmethyl)cyclohexanone (corresponding to 83% of the theoretically calculated yield) were obtained.

2nd step: 2-(dimethylaminophenylmethyl)-1-(3-trifluoromethylbenzyl)cyclohexanol hydrochloride 0.38 g (15.6 mmol) of magnesium chips were stirred into 10 ml of analytically pure diethyl ether. 3.03 g (15.6 mmol) of 3-chloromethyl benzotrifluoride, dissolved in 10 ml of diethyl ether, were added dropwise in such a manner that the reaction mixture boiled slightly. After the addition, stirring was continued for one hour at room temperature. 3.00 g (13.0 mmol) of the 2-(dimethylaminophenylmethyl)cyclohexanone prepared according to step 1 were dissolved in 15 ml of diethyl ether, added dropwise to the Grignard batch while cooling with an ice-bath, and stirred for 15 hours at room temperature.

For working up, 20 ml of saturated ammonium chloride solution were added while cooling with an ice-bath, and the mixture was extracted three times at room temperature using 20 ml of diethyl ether each time. The combined organic extracts were dried over sodium sulfate, filtered and concentrated in a rotary evaporator (from 500 to 10 mbar). 4.90 g of crude base (corresponding to 96% of the theoretically calculated yield) were obtained, from which there were obtained according to Example 1 (2nd step), using chlorotrimethylsilane/water in 2-butanone, 3.16 g of 2-(dimethylaminophenylmethyl)-1-(3-trifluoromethylbenzyl)cyclohexanol hydrochloride (corresponding to 57% of the theoretically calculated yield) having a melting point of 184–186° C.

Example 6

1st Step:
[2-dimethylaminothiophen-2-ylmethyl]cyclohexanone 4.36 g (53.5 mmol) of freshly dried dimethylamine hydrochloride were added, with stirring, to 118 ml (118 mmol) of sodium iodide solution (1 M in acetonitrile), cooled to 0° C. with an ice-bath; 15 ml (107 mmol) of triethylamine and 15 ml (118 mmol) of chlorotrimethylsilane were added dropwise, and the mixture was then stirred for one hour at room temperature. While cooling with ice, 6.0 g (53.5 mmol) of thiophene-2-carboxaldehyde were added, and stirring was carried out for a further one hour at room temperature. The mixture was again cooled to 0° C. with an ice-bath, 8.6 ml (53.5 mmol) of 1-(pyrrolidino)-1-cyclohexene were added, and the mixture was stirred for a further two hours at room temperature. For working up, 80 ml of semi-concentrated hydrochloric acid were added to the batch while cooling with ice, and the mixture was stirred for 10 minutes, washed twice with 80 ml of ether each time, and rendered alkaline (pH approximately 9) with 200 ml of dilute ammonia solution (5 vol. %). The mixture was extracted three times using 80 ml of ether each time, and the combined organic extracts were dried over sodium sulfate, filtered and concentrated in a rotary evaporator (from 500 to 10 mbar). 8.09 g of crude base of 2-(dimethylaminothiophen-2-ylmethyl)cyclohexanone (63.7% of the theoretical yield) were obtained.

2nd Step 2-(dimethylaminothiophen-2-ylmethyl)-1-(3-trifluoromethylbenzyl)cyclohexanol Hydrochloride 0.31 g (12.6 mmol) of magnesium chips were stirred into 10 ml of analytically pure diethyl ether. 2.46 g (12.6 mmol) of 3-chloromethyl benzotrifluoride, dissolved in 10 ml of ether, were added dropwise in such a manner that the reaction mixture boiled slightly. When the addition was complete, stirring was continued for one hour at room temperature. 2.50 g (10.5 mmol) of the 2-(dimethylaminothiophen-2-ylmethyl)cyclohexanone prepared according to step 1 were dissolved in 10 ml of ether, added dropwise to the Grignard batch while cooling with an ice-bath, and stirred for 15 hours at room temperature. For working up, 15 ml of saturated ammonium chloride solution were added while cooling with an ice-bath, and the mixture was extracted three times at room temperature using 20 ml of ether each time. The combined organic extracts were dried over sodium sulfate, filtered and concentrated in a rotary evaporator (from 500 to 10 mbar). 3.33 g of crude base (corresponding to 79.6% of the theoretically calculated yield) were obtained, from which a hydrochloride was precipitated according to Example 1 (3rd step) using chlorotrimethylsilane/water in 2-butanone. The base was freed therefrom using 20 ml of water and 5 ml of ammonia solution (25 vol. %) and extracted three times using 20 ml of ether each time, and the combined organic extracts were dried over sodium sulfate, filtered and concentrated in a rotary evaporator (from 500 to 10 mbar). 0.63 g of crude base (15.0% of the theoretical yield) was obtained, from which there was obtained according to Example 1 (2nd step), using chlorotrimethylsilane/water in 2-butanone, 0.39 g of 2-[dimethylaminothiophen-2-ylmethyl]-1-(3-trifluoromethylbenzyl)cyclohexanol hydrochloride (8.5% of the theoretical yield), which decomposes at 98° C. and above.

Example 7

2-(dimethylaminothiophen-3-ylmethyl)-1-(3-trifluoromethylbenzyl)cyclohexanol hydrochloride In the manner described for Example 6, 2-(dimethylaminothiophen-3-ylmethyl)cyclohexanone was first prepared from dimethylamine hydrochloride, thiophene-3-carbaldehyde and 1-(pyrrolidino)-1-cyclohexene and then, by reaction with 3-chloromethyl benzotrifluoride in a Grignard reaction and subsequent precipitation of the hydrochloride, 2-(dimethylaminothiophen-3-ylmethyl)-1-(3-trifluoromethylbenzyl)cyclohexanol hydrochloride was obtained.

Molecular-Pharmacological Investigations:

For each of the compounds of Examples 1 to 7, the affinity for the ORL1 receptor was determined according to the mentioned molecular-pharmacological investigations. The corresponding $K_i$ values are given in Table 1 below.

TABLE 1

| Example | $K_i$ ($\mu$M) ORL1 binding assay |
|---|---|
| 1 | 6.0 |
| 2 | 2.1 |
| 3 | 1.7 |
| 4 | 1.9 |
| 5 | 0.90 |

TABLE 1-continued

| Example | $K_i$ ($\mu$M) ORL1 binding assay |
|---|---|
| 6 | 0.60 |
| 7 | 0.33 |

What is claimed is:

1. A method for regulating the ORL1 receptor of the nociception/orphanin FQ ligand-ORL1 receptor system, comprising:
   administering a pharmaceutical composition comprising at least one substituted 4-amino-1-phenylbutan-2-ol compound of formula I

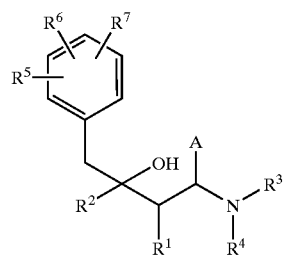

wherein
   the radical A represents substituted or unsubstituted phenyl,
   the radicals $R^1$ and $R^2$, form a $(CH_2)_{2-6}$ ring, which may also be substituted by phenyl,
   the radicals $R^3$ and $R^4$, which may be identical or different, represent a $C_{1-6}$-alkyl radical,
   the radicals $R^5$, $R^6$ and $R^7$, which may be identical or different, represent H, F, Cl, Br, I, $CF_3$, $OR^8$, $SO_2CF_3$, phenyl, CN, $NO_2$ or a $C_{1-6}$-alkyl radical, the radical $R^8$ represents H, or a $C_{1-6}$-alkyl radical,
   in the form of a racemate, an enantiomer, a diastereomer, base, or salt of a physiologically tolerable acid, and pharmaceuticallyu acceptable acceptable diluent or carrier to a human in need of regulation of the ORL1receptor of the nociceptin/orphanin FQ ligand-ORL1 receptor system for the treatment of anxiolysis.

2. The method of claim 1, wherein A is a phenyl, that is substituted with at least one radical selected from the group consisting of $OR^8$, F, Cl, Br, CN, $NO_2$, $C_{1-6}$-alkyl or phenyl.

3. The method of claim 1, wherein $R^5$ to $R^7$ which may be identical or different, represent H, a halogen or $CF_3$.

4. The method of claim 1, wherein the compound is
   1-(2-chlorobenzyl)-2-(dimethylaminophenylmethyl)cyclohexanol,
   1-(3-chlorobenzyl)-2-(dimethylaminophenylmethyl)cyclohexanol,
   1-(4-chlorobenzyl)-2-(dimethylaminophenylmethyl)cyclohexanol,
   1-(3,4-difluorobenzyl)-2-(dimethylaminophenylmethyl)cyclohexanol, or
   2-(dimethylaminophenylmethyl)-1-(3-trifluoromethylbenzyl)cyclohexanol,
   or a hydrochloride thereof.

5. The method of claim 1, wherein in said compound, the radicals $R^3$ and $R^4$ represent a $C_{1-3}$-alkyl radical.

6. The method of claim 1, wherein in said compound, the radical $R^8$ represents a $C_{1-3}$-alkyl radical.

* * * * *